United States Patent [19]

Edwards et al.

[11] Patent Number: 5,403,306

[45] Date of Patent: Apr. 4, 1995

[54] LASER SURGERY METHOD

[75] Inventors: Glenn S. Edwards; Regan A. Logan; Denis M. O'Day; Michael Copeland, all of Nashville, Tenn.

[73] Assignee: Vanderbilt University, Nashville, Tenn.

[21] Appl. No.: 80,915

[22] Filed: Jun. 22, 1993

[51] Int. Cl.⁶ .............................................. A61N 5/06
[52] U.S. Cl. ............................................. 606/3; 606/2
[58] Field of Search .................... 606/2, 3, 9, 14, 15, 606/16

[56] References Cited

U.S. PATENT DOCUMENTS

| | | | |
|---|---|---|---|
| 3,769,963 | 9/1973 | Goldman et al. | 128/303 |
| 4,633,866 | 1/1987 | Peyman et al. | 128/303 |
| 4,852,567 | 8/1989 | Sinofsky | 128/303 |
| 4,854,320 | 8/1989 | Dew et al. | 606/3 |
| 4,917,084 | 4/1990 | Sinofsky | 606/3 |
| 4,963,142 | 10/1990 | Loerstscher | 606/15 |
| 5,066,291 | 11/1991 | Stewart | 606/3 |
| 5,139,494 | 8/1992 | Freiberg | 606/3 |

FOREIGN PATENT DOCUMENTS 1073914  6/1985  U.S.S.R. .................... 606/10

Primary Examiner—David M. Shay
Assistant Examiner—Sonya C. Harris
Attorney, Agent, or Firm—Waddey & Patterson

[57] ABSTRACT

A laser surgery method is disclosed for use in efficient ablation of tissue with little or no thermal damage to adjacent tissues. The wavelength of the surgical laser is tuned to an absorption peak of a proteinaceous material or functional groups contained therein, the amides for example. A suitable power level is chosen to either vaporize or liquify the targeted tissue.

5 Claims, 8 Drawing Sheets

LASER SURGERY METHOD

This invention was made with government support under grant number N00014-91-C0109 from the Office of Naval Research. The United States government has certain rights in the invention.

Be it known that we, Glenn S. Edwards, a citizen of the United States, residing at 2106 25th Avenue South, Nashville, Tenn., 37212; Regan A. Logan, a citizen of the United States, residing at 2725 W. Linden Avenue, Nashville, Tenn., 37212; Denis M. O'Day, a citizen of Australia, residing 1206 Nichol Road, Nashville, Tenn., 37203; and Michael Copeland, a citizen of the United States, residing at 213 Andover Way, Nashville, Tenn., 37221, have invented a new and useful "Laser Surgery Method".

BACKGROUND OF THE INVENTION

The present invention relates generally to the use of laser radiation as a therapeutic tool in medicine and surgery, and more particularly to the use of an infrared laser in the precision surgical ablation or cutting of tissue under conditions where minimization of damage to adjacent non-targeted tissues is required.

Laser technology is currently used in clinical medical practice in a variety of applications, including as a surgical tool for the therapeutic ablation of human tissues, both internal and external. In some applications, the precision obtainable by a narrowly and accurately focused beam of laser radiation is superior to other more traditional surgical techniques. However, the use of lasers in certain areas, such as in the eye or brain, carries also the risk of thermal damage being done to sensitive tissues adjacent to the areas where tissue incision or removal is desired.

Although prior art laser surgery techniques have recognized the problems of thermal damage to healthy tissues during laser surgery, none of the proposed solutions have been entirely satisfactory. A principal deficiency is that prior art laser surgery techniques have not employed the optimum non-photochemical wavelengths of laser radiation which produce ablation without thermal damage. The infrared (IR) region has been preferred over ultraviolet (UV) in many surgical applications because the IR wavelengths are non-photochemical in their effect on tissue and because laser radiation at some UV wavelengths has been reported to cause cell mutation.

For example, $CO_2$ lasers are in common surgical use and have a nominal operating wavelength of 10.6 microns. Unfortunately, experience has demonstrated that thermal damage to healthy adjacent tissue is a predictable consequence of the use of a $CO_2$ laser to ablate tissue. Although selection of an appropriate pulse structure and duty cycle can improve the effectiveness of $CO_2$ lasers in some applications, the damaged areas cannot be eliminated.

Other investigators and practitioners have used Er:YAG or other solid state lasers in the infrared range, often tuned to a wave length which is known to correspond to an energy absorption band of water, at 2.94 microns for example. The theory behind methods which use such laser wavelengths is that because human tissue is approximately eighty percent (80%) water, the interaction of laser energy in water will also characterize the response of human tissues to infrared radiation of the same wavelength. The O—H stretch mode of water, which corresponds to 2.94 microns, is the most efficient absorber of IR radiation. This theory (and these prior art methods), however, fail to take into account and properly compensate for the method of energy transfer into a biomaterial, in this case human or animal tissue, which universally includes one or more proteins and related structures which both confine and are affected by water vaporization.

Thus, the use of a laser surgery method which maximizes transfer of energy into the water component of human tissue by targeting the O—H stretch or other vibrational modes of water may produce rapid and effective ablation of tissue. The problem of heating of water and consequent thermal and dynamic effects on the structure of adjacent tissues remains. Accordingly, those experienced in the art have reported that ablation of tissue using a laser tuned to 2.94 microns is achieved by an explosive mechanism involving rapid heating, vaporization, and subsequent high-pressure expansion of irradiated tissue. It is believed, then, that this mechanism can cause thermal damage to collateral tissues from the hot gases produced, and tearing of those same tissues by pressures exerted by both the expanding gases and liquified or vaporized tissue from the target area. Similar thermal and mechanical effects have been reported at shorter wavelengths and at 10.6 microns. This ablation mechanism is particularly undesirable in situations, such as in delicate eye surgery, where precision liquification and extraction of tissue is preferred over explosive vaporization.

What is needed, then, is a laser surgery method which can efficiently and precisely ablate a variety of human tissue types with controllable, and is some cases, little or no discernable thermal or mechanical damage to non-targeted adjacent tissues. Such a method is presently lacking in the prior art.

SUMMARY OF THE INVENTION

In the method of the present invention, a pulsed infrared laser is tuned to a wavelength which corresponds to a vibrational mode of protein in human tissue, and specifically to one or more of the specific wavelengths known to target different amide bands found in all proteinaceous material. A preferred laser power level, pulse structure, and beam size is selected and applied to the targeted tissue using a conventional focusing lens and/or laser catheter system. The targeted tissue is then vaporized, leaving relatively intact and undamaged the non-targeted tissues immediately adjacent to the area of ablation. The laser wavelength can be adjusted to allow for a procedure in which tissue liquification and removal is preferable to vaporization, or to enhance other clinical effects such as increased hemostasis, if desired.

An object of the present invention, then, is to provide a laser surgery method of ablating tissue which can efficiently remove or liquify targeted tissue without causing significant damage to adjacent tissues.

Another object of the present invention is to provide a method of laser surgery which controls the partitioning of energy between protein and water and does not focus solely on an energy absorption peak of water.

A further object of the present invention is to provide for a laser surgery technique which is effective in ablating a wide variety of tissues using a single infrared laser wavelength.

DESCRIPTION OF THE PREFERRED EMBODIMENT

In all human and animal tissues, certain functional groups are universally found in all proteinaceous materials regardless of the tissue type or location. One such functional group is the organic amides, whose characteristic molecular structure is $R_1CONR_2$, where $R_1$ and $R_2$ are amino acid side chains, $CH_3$ for example. Experimental evidence in the prior art indicates that these proteinaceous amides (and other bio-polymers) exhibit a series of discrete vibrational modes of peak infrared energy absorption. It is believed that each such mode corresponds to a stretching (symmetric or asymmetric) or bending (in plane or out of plane) vibration of a specific set of bands in the protein. These amide vibrational modes and associated infrared radiation absorption peaks have been identified and assigned conventional reference names, as set forth in Table 1 below.

TABLE 1

| Frequency Range of Vibrational Modes in Biopolymers | | | |
|---|---|---|---|
| | Frequency Range | | |
| Band | (cm-1) | (microns) | Assignment |
| Amide A | 3300 | 3.0 | N—H |
| Amide B | 3100 | 3.3 | N—H (Fermi resonance) |
| Amide I | 1670 | 6.0 | C=O, N—H, C—N |
| Amide II | 1560 | 6.4 | C—N, N—H |
| Amide III | 1300 | 7.7 | C—N, N—H |
| Amide IV | 625 | 16.0 | O=C—N |
| Amide V | 725 | 13.8 | N—H |
| Amide VI | 600 | 16.7 | C=O |
| Amide VII | 200 | 50.0 | C—N |

Figure 1:
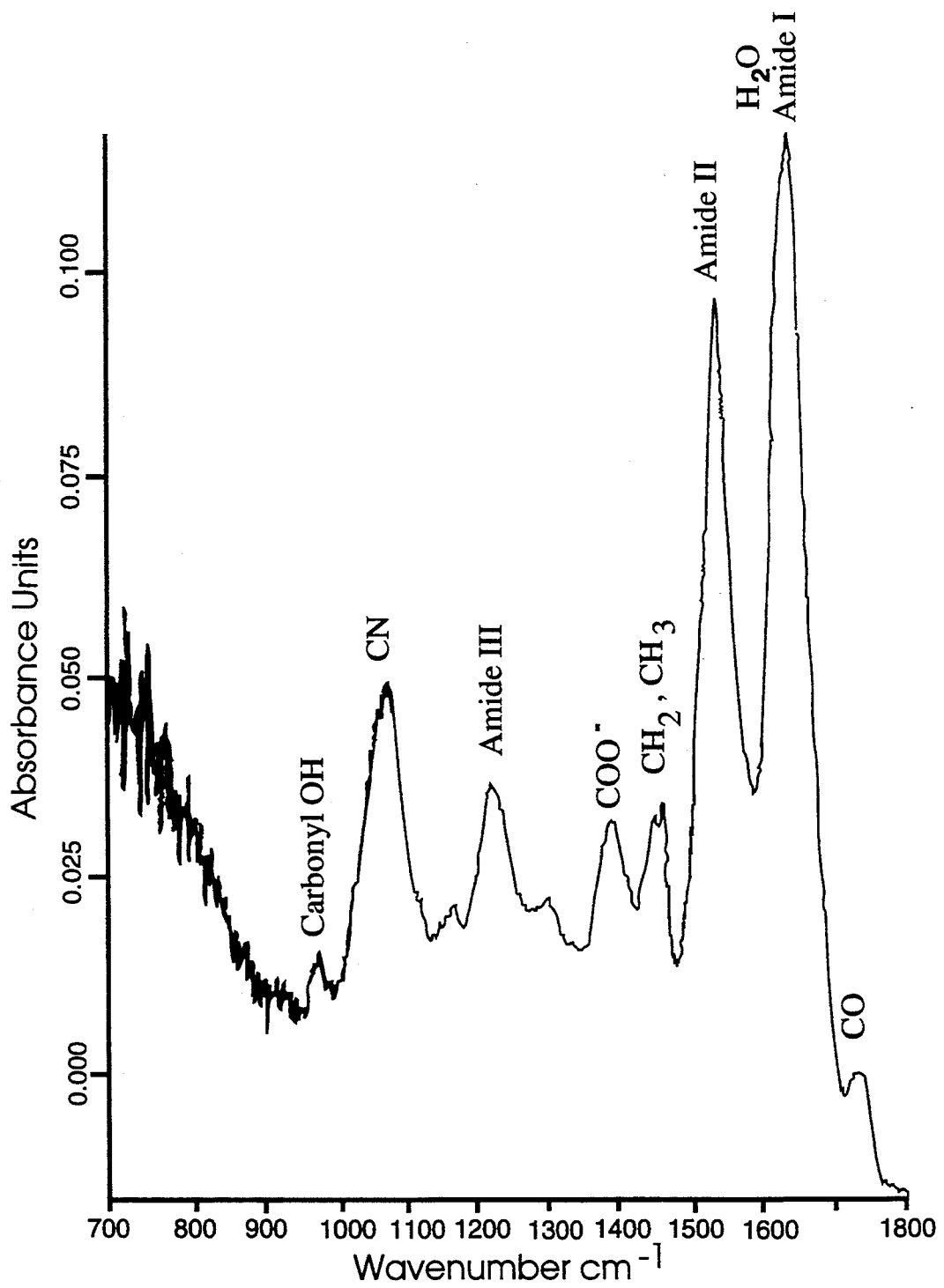
FIG. 1 is a graphical representation of the relative absorbance of infrared radiation by brain tissue as a function of frequency.
Figure 2:
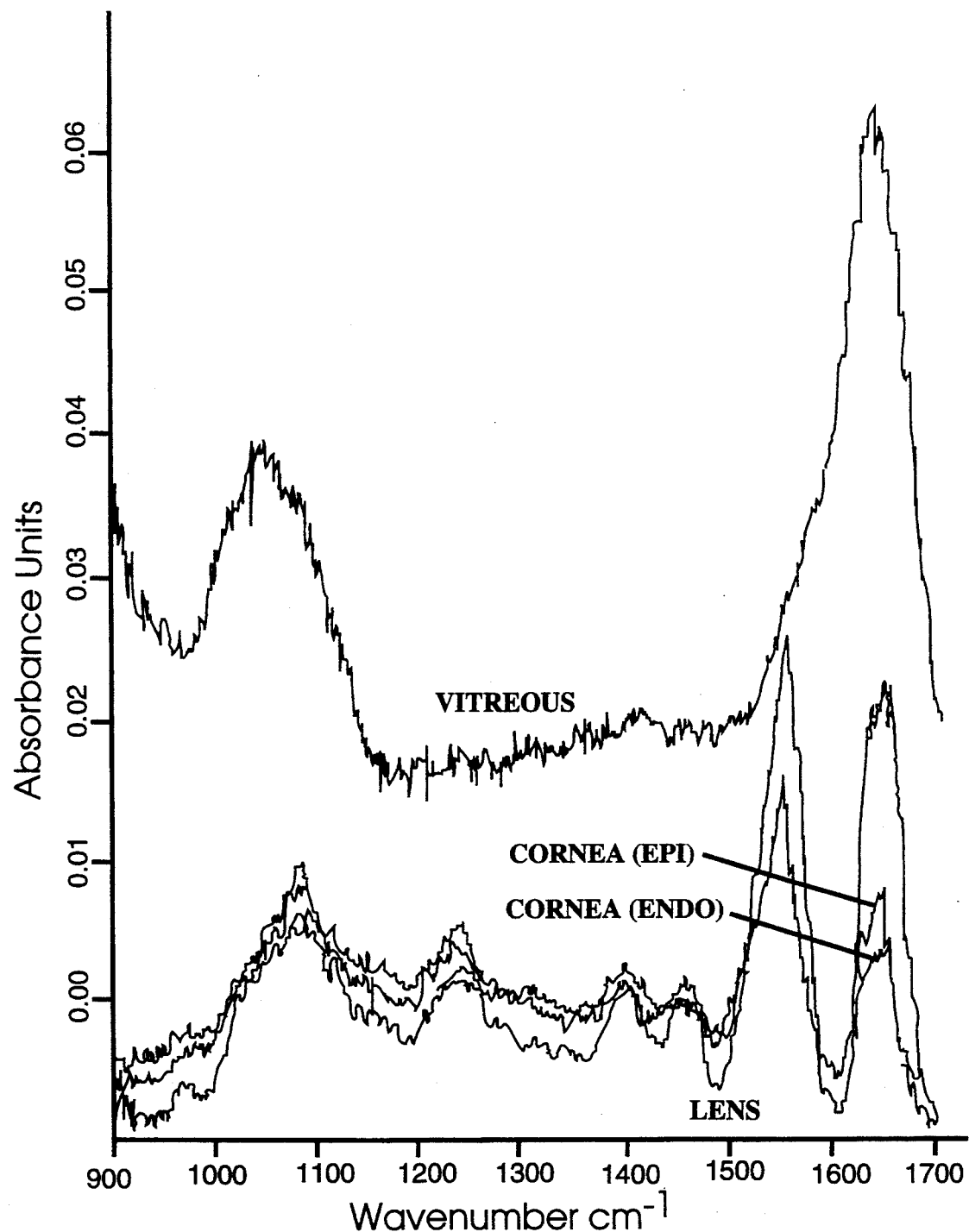
FIG. 2 is a graphical representation of the relative absorbance of infrared radiation by vitreous, epithelial corneal, endothelial corneal, and lens ocular tissues as a function of the laser frequency.
Figure 3:
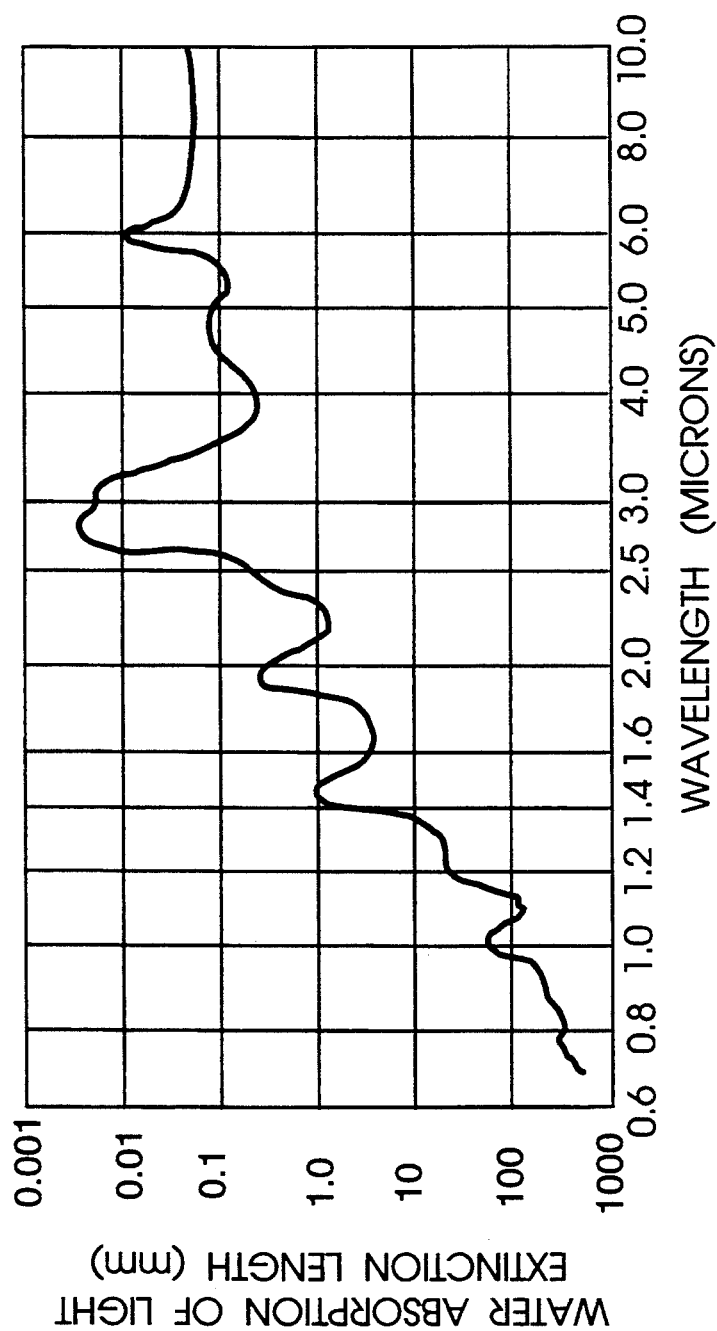
FIG. 3 is a graphical representation of the relative absorbance of infrared radiation by water as a function of the wavelength.

These energy absorption peaks have been confirmed experimentally using neural and ocular tissue subjected to radiation from a Fourier transform infrared spectrometer. FIG. 1 shows the relative IR absorption of sheep brain tissue as a function of laser radiation wave number, where wave number is the inverse of the wavelength. Specific absorption peaks are observed at the Amide I, II, and III bands. The energy absorption peak of Amide I (6.0 microns) is very close to a bending mode of pure water (6.1 microns), as seen on FIGS. 1, 3 and 4. FIG. 2 shows similar results using four different types of ocular tissue.

Figure 9:
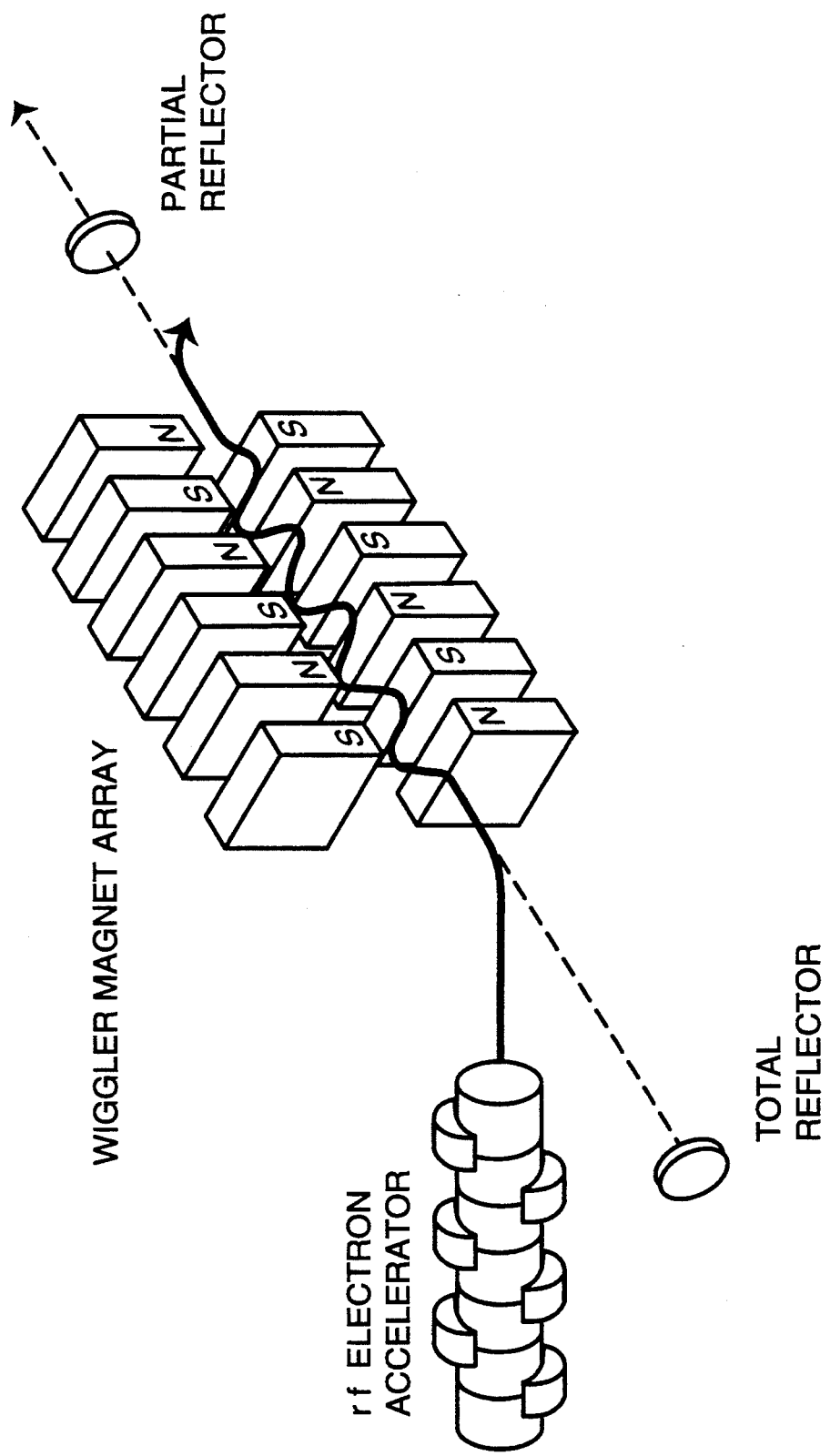
FIG. 9 is a schematic view of a free electron laser system as used in the method of the present invention.
Figure 10:
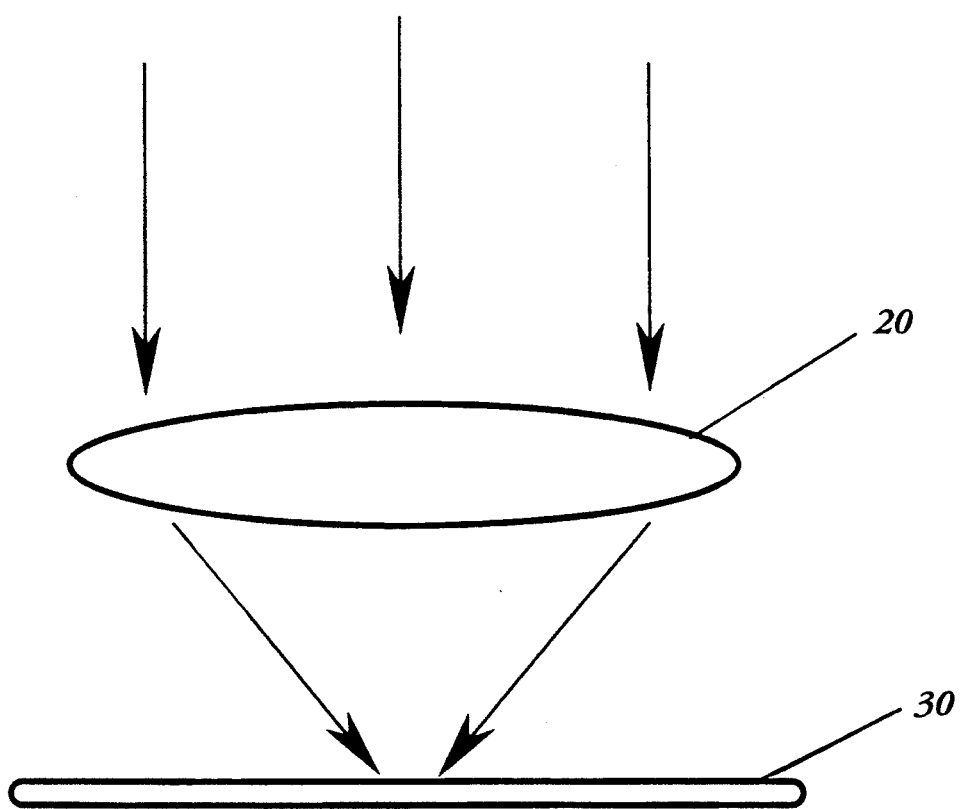
FIG. 10 is a side view showing the beam size and focusing lens as used in the method of the present invention.

Accordingly, and looking now at FIGS. 9 and 10, to carry out the method of the present invention, a laser 10 (FIG. 9), in this case an FEL, is positioned so as to be focused on the tissue 30 to be ablated through a conventional fluoride lens 20, although any laser beam focusing or catheter system can be used. Tissue 30 is positioned at a distance approximately 10 to 20 cm from lens 20. Laser 10 is then tuned to correspond to one or more of the wavelengths of peak absorption of an amide band. The diameter of the focused laser beam is then adjusted according to the specific clinical application. A preferred laser pulse structure and power level is then selected and programmed into laser 10 in a conventional manner. As used herein, ablation can include cutting, liquification, or vaporization of tissue.

In a first embodiment of the method of the present invention, the wavelength of laser 10 is adjusted to 6.45 microns, corresponding to the energy absorption peak of the Amide II vibration mode. Tissue 30, in this embodiment brain tissue, is then subjected to 100 macropulses at a pulse frequency of 4 HZ, with a power density of approximately 10 millijoules per macropulse. For purposes of the method of the present invention, using an FEL, a macropulse consists of a train of approximately $10^4$ micropulses, with each micropulse having an average duration of approximately one picosecond and with approximately 350 picoseconds between each micropulse, such that each macropulse has a duration of approximately 6 microseconds.

Figure 5:
FIG. 5 is a microscopically enlarged cross-sectional view of a segment of brain tissue following use of a prior art laser surgery method.
Figure 6:
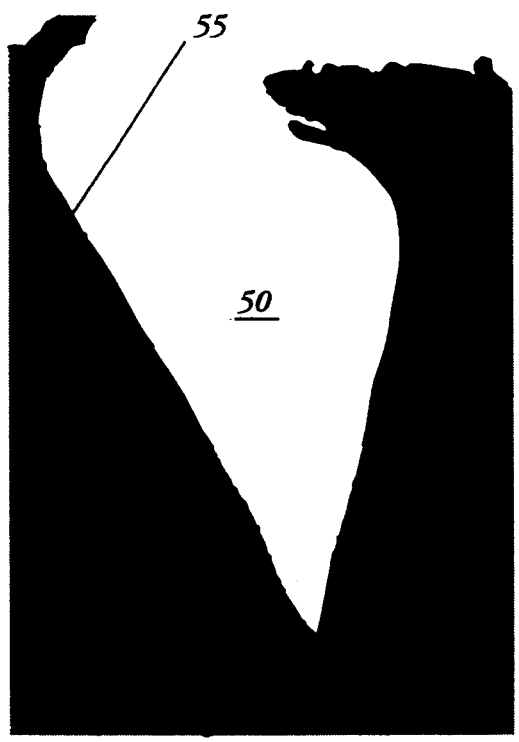
FIG. 6 is a microscopically enlarged cross-sectional view of a segment of brain tissue following use of the method of the present invention.

Looking now at FIG. 6, the results of using the laser energy method of the present invention to ablate neural tissue is shown. The cone shaped area 50 of ablated tissue is defined by relatively smooth vertical walls 55, approximately 2.3 mm deep. Using a beam diameter of approximately 20 microns, the diameter of the opening at ablated area 50 is approximately 1.5 millimeters. FIG. 6 shows an absence of perceptible coagulation necrosis. FIG. 5 shows the results from using a laser surgery method on similar tissue, but with the laser tuned to 2.5 microns, a wavelength commonly used in prior art methods. After exposing the neural tissue to 100 macropulses at a duty cycle of 4 HZ, with a power density of approximately 20 mJ per macropulse, considerable coagulation necrosis (indicated by the loss of cellular markings) is found from the surface to beyond the trough of the incision.

Figure 7:
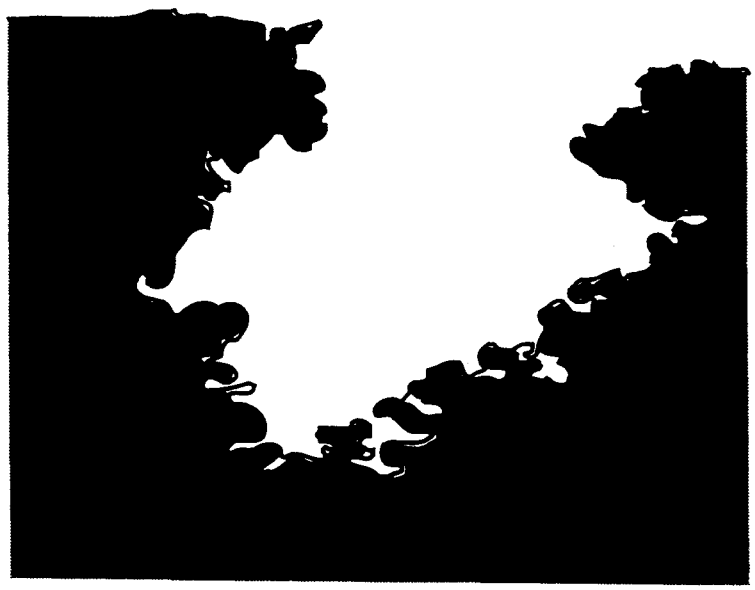
FIG. 7 is a cross sectional view of a segment of corneal tissue following use of a prior art laser surgery method.
Figure 8:
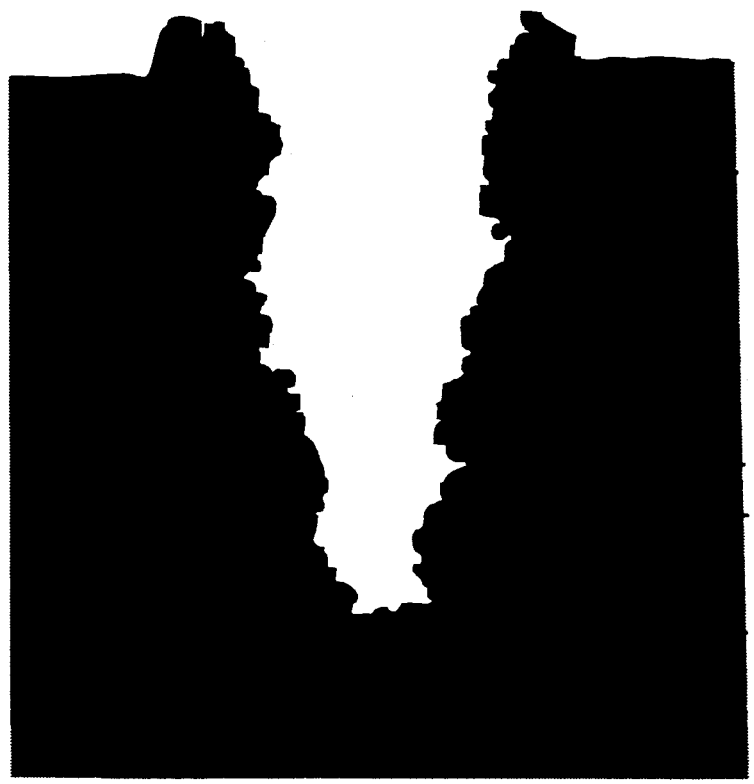
FIG. 8 is a cross-sectional view of a section of corneal tissue following use of the method of the present invention.

In another application of this first embodiment, as seen on FIG. 8, laser ablation of corneal tissue using the method of the present invention is shown. After the FEL is tuned to 6.45 microns, one macropulse of radiation, having a power density of approximately 20 mJ, is directed to the surface of the tissue. The quality of incisions was superior and the amount of tissue denaturation was reduced at a wavelength of 6.45 micrometers compared to other wavelengths. This type of ablation would be clinically useful in corneal refractive surgery, removal of superficial tumors of the cornea and conjunctiva, and could also improve the optical quality of corneal grafts. In contrast, FIG. 7 shows the results achieved by laser surgery ablation using a prior art wavelength of 3.0 microns, after a one macropulse (36 mJ power density) exposure. It is estimated that, in this first embodiment, at least twenty percent (20%) of the energy transferred to the tissue to be ablated is absorbed by protein in the tissue.

In a second embodiment of the method of the present invention, tuning laser 10 to a wavelength other than 6.45 microns (the amide II absorption peak) can be of clinical benefit as well, while still minimizing collateral tissue damage. For example, tuning to the absorption peak represented by the Amide III vibrational mode (approximately 7.7 microns) can allow the practitioner to liquify without vaporizing the tissue. Such liquified tissue is then available for conventional suction removal. This can be advantageous in certain delicate eye surgeries, for example. In this second embodiment, after the laser is tuned to 7.7 microns, the beam will be delivered to intra-ocular structures such as cataractous lens nucleus, or intraocular tumors, via waveguides or fiber-optics inserted surgically into the eye and lens. Following liquification, diseased tissue will be removed with standard intraocular aspiration techniques. In this second embodiment, substantially all (greater than 99%) of the energy transferred to the tissue is absorbed by protein in the tissue rather than water.

Also, tuning laser 10 to the absorption peak represented by the Amide I band, which is near an absorption peak of water, should produce a somewhat enhanced thermal effect from water vaporization. Such limited thermal effect can be helpful in achieving good hemostasis where needed.

Figure 4:
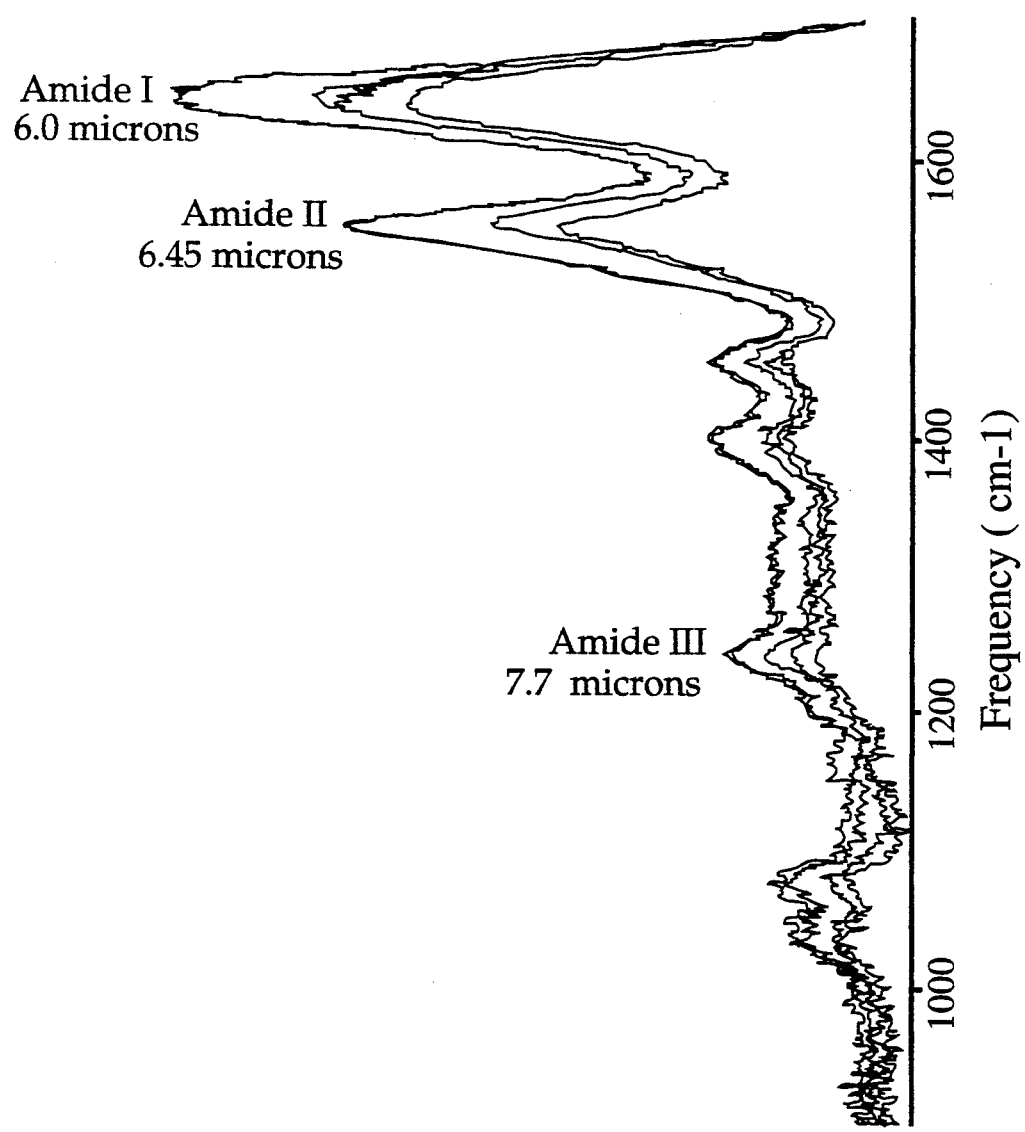
FIG. 4 is a graphical representation of the relative absorbance of IR radiation by brain tissue as a function of frequency.

In yet other applications, laser 10 can be tuned proximate to but slightly away from a wavelength corresponding to an amide band, such that the IR wavelength falls on a "wing" of an absorption peak rather than directly on the peak itself (see FIG. 4). With such slight "de-tuning", a variation in the ratio of energy being transferred to protein in the tissue as compared to water in the tissue can be effected. In such applications, as long as the de-tuned or "wing" wavelength does not fall on an absorption peak of water, the improved clinical results of the present invention can still be achieved.

Other wavelengths corresponding to energy absorption peaks of different proteinaceous structures, or functional groups in proteins, even those other than the amide functional groups, may also be of benefit in particular clinical applications.

Also, the laser surgery method described and claimed herein is not limited to use with a free electron laser. For example, a more conventional solid state laser or optical parametric oscillator can be manufactured and tuned to a fixed wavelength, 6.45 microns for example, and thereby be useful as a tool for tissue ablation in a variety of applications. It would also be within the scope of the present invention to simultaneously irradiate tissue with multiple laser beams of different wavelengths, each of which could be targeted to a different proteinaceous material absorption peak, for example.

Thus, although there have been described particular embodiments of the present invention of a new and useful laser surgery method, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What we claim is:

1. A method of ablating human or animal tissue, said method comprising directing a beam of radiation from said laser at said tissue to be ablated, said laser radiation having a wavelength which approximately corresponds to an energy absorption peak of at least one amide band of said tissue, said amide band selected from the group consisting of Amide I, Amide II, and Amide III.

2. A method of ablating tissue comprising the steps of:
   a. aiming a source capable of producing laser radiation at said tissue to be ablated; and
   b. operating said source at a wavelength wherein said radiation wavelength is approximately 6.45 microns.

3. A method of ablating tissue comprising the steps of:
   a. aiming a source capable of producing laser radiation at said tissue to be ablated; and
   b. operating said source at a wavelength wherein said radiation wavelength is approximately 6.0 microns.

4. A method of ablating tissue comprising the steps of:
   a. aiming a source capable of producing laser radiation at said tissue to be ablated; and
   b. operating said source at a wavelength wherein said radiation wavelength is approximately 7.7 microns.

5. A method of liquefying tissue comprising the steps of:
   a. aiming a source capable of producing laser radiation at said tissue to be liquified;
   b. operating said source at a radiation wavelength of 7.7 microns;
   c. exposing said tissue to said radiation for a duration and at an energy level sufficient to liquify but not vaporize said tissue, and without causing significant thermal damage to adjacent tissues; and
   d. removing said liquefied tissue.

* * * * *